(12) United States Patent
Zhao et al.

(10) Patent No.: US 10,113,969 B2
(45) Date of Patent: *Oct. 30, 2018

(54) METHODS AND DEVICES FOR MEASURING RAMAN SCATTERING OF A SAMPLE

(71) Applicant: B&W TEK LLC, Newark, DE (US)

(72) Inventors: Jun Zhao, The Woodlands, TX (US); Xin J. Zhou, Hockessin, DE (US)

(73) Assignee: B&W TEK LLC, Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,510

(22) Filed: Nov. 11, 2016

(65) Prior Publication Data
US 2018/0136131 A1 May 17, 2018

(51) Int. Cl.
*G01N 21/65* (2006.01)
*G01N 21/49* (2006.01)

(52) U.S. Cl.
CPC ............ *G01N 21/65* (2013.01); *G01N 21/49* (2013.01); *G01N 2021/651* (2013.01); *G01N 2201/065* (2013.01); *G01N 2201/08* (2013.01)

(58) Field of Classification Search
CPC ............ G01N 21/65; G01N 2021/656; G01N 2201/068; G01N 2201/08; G01J 3/0216; G01J 3/44–2003/4244
(Continued)

(56) References Cited

U.S. PATENT DOCUMENTS 4,076,421 A    2/1978  Kishner
4,378,159 A *  3/1983  Galbraith ........... G01N 21/8901
                                              356/236

(Continued)

FOREIGN PATENT DOCUMENTS

DE    26 06 675    9/1977
DE    32 23 876    1/1983
(Continued)

OTHER PUBLICATIONS

English-language translation of German Office Action of German Application No. 102016225808.7, dated Nov. 24, 2017.

*Primary Examiner* — Michael P Lapage
(74) *Attorney, Agent, or Firm* — Blank Rome LLP

(57) ABSTRACT

This invention relates to a light delivery and collection device for measuring Raman scattering from a large area of a sample. The light delivery and collection device comprises a reflective cavity made of a material or having a surface coating with high reflectivity to the excitation light and the Raman scattered light. The reflective cavity has two apertures. The first aperture is configured to receive the excitation light which then projects onto the second aperture. The second aperture is configured to be applied close to the sample such that the reflective cavity substantially forms an enclosure covering a large area of the sample. The excitation light produces Raman scattered light from the covered area of the sample. The reflective cavity reflects any excitation light and Raman light scattered from the sample unless the excitation light and the Raman scattered light either emit from the first aperture to be measured with a spectrometer device, or are re-scattered by the sample at the second aperture. The multi-reflection of the reflective cavity greatly improves the excitation efficiency of Raman scattering from the sample and in the meantime enhances its collection efficiency. In addition, it also causes more excitation light to penetrate into a diffusely scattering sample and allows efficient collection of the Raman scattered light generated thereof, hence enabling sub-surface Raman scattering measurement.

17 Claims, 9 Drawing Sheets

(58) Field of Classification Search
USPC .......................................................... 356/445
See application file for complete search history.

(56) References Cited

U.S. PATENT DOCUMENTS

| | | | |
|---|---|---|---|
| 4,645,340 A | 2/1987 | Graham et al. | |
| 4,853,542 A | 8/1989 | Milosevic et al. | |
| 4,988,205 A | 1/1991 | Snail | |
| 5,112,127 A | 5/1992 | Carrabba et al. | |
| 5,199,431 A * | 4/1993 | Kittrell | A61B 1/00096 600/476 |
| 5,280,788 A * | 1/1994 | Janes | A61B 5/0084 600/476 |
| 5,517,315 A * | 5/1996 | Snail | G01N 21/474 250/339.07 |
| 5,615,673 A * | 4/1997 | Berger | A61B 5/14532 356/301 |
| 5,659,397 A | 8/1997 | Miller et al. | |
| 5,864,397 A * | 1/1999 | Vo-Dinh | G01J 3/44 356/301 |
| 6,370,406 B1 * | 4/2002 | Wach | G01N 21/474 356/301 |
| 6,781,697 B1 * | 8/2004 | Carra | G01N 21/57 356/236 |
| 7,148,963 B2 | 12/2006 | Owen et al. | |
| 7,652,763 B2 | 1/2010 | Matousek et al. | |
| 7,671,985 B1 * | 3/2010 | Milosevic | G01N 21/474 356/301 |
| 8,248,600 B2 | 8/2012 | Matousek et al. | |
| 2004/0263842 A1 * | 12/2004 | Puppels | G01N 21/65 356/301 |
| 2012/0089030 A1 * | 4/2012 | Guze | A61B 5/0088 600/476 |
| 2013/0038869 A1 | 2/2013 | Lascola et al. | |
| 2016/0209388 A1 | 7/2016 | Yakovlev et al. | |

FOREIGN PATENT DOCUMENTS

| | | |
|---|---|---|
| DE | 33 11 954 | 2/1992 |
| DE | 693 13 633 | 4/1998 |
| DE | 11 2006 000 273 | 1/2013 |
| DE | 10 2012 101 744 | 9/2013 |
| WO | WO-98/22802 | 5/1998 |
| WO | 2004/031749 A2 | 4/2004 |
| WO | WO-2015/114379 | 8/2015 |

* cited by examiner

Raman Shift (cm-1)

Raman Shift (cm-1)

Raman Shift (cm-1)

METHODS AND DEVICES FOR MEASURING RAMAN SCATTERING OF A SAMPLE

FIELD OF THE INVENTION

This invention generally relates to a light delivery and collection device, and more specifically to a light delivery and collection device for measuring Raman scattering of a sample.

BACKGROUND

Raman spectroscopy is an optical spectroscopy technique, which measures the inelastic scattering, i.e. Raman scattering of monochromatic light by a material to produce a spectrum characteristic of the material. Raman spectroscopy has been demonstrated to be a powerful non-invasive analytical technology for material characterization and identification.

Conventional Raman spectroscopy generally utilizes a well-focused laser beam to produce Raman scattering signal from the sample. This approach has the apparent advantage of relatively high efficiency in Raman signal excitation and collection. However, it also suffers from the following drawbacks. First, only a small volume of the sample is measured. Thus the collected Raman spectrum may not be very representative, especially for some non-uniform samples. Second, the tightly focused laser beam may cause damage to some delicate samples. Third, for diffusely scattering samples which are not transparent to the laser beam, this approach will only measure the Raman scattering signal from the surface layer of the sample. The majority of the material underneath the surface will be almost completely out of reach. There thus exists a need for an improved light delivery and collection device for performing Raman spectroscopy, which not only allows the measurement of a large area of the sample but also enables sub-surface Raman signal excitation and collection.

SUMMARY OF THE INVENTION

It is the object of the present invention to provide a light delivery and collection device for measuring Raman scattering from a large area of a sample. The light delivery and collection device comprises a reflective cavity made of a material or having a surface coating with high reflectivity to the excitation light and the Raman scattered light. The reflective cavity has two apertures. The first aperture is configured to receive the excitation light which then projects onto the second aperture. The second aperture is configured to be applied close to the sample such that the reflective cavity substantially forms an enclosure covering a large area of the sample. The excitation light produces Raman scattered light from the covered area of the sample. The reflective cavity reflects any excitation light and Raman light scattered from the sample unless the excitation light and the Raman scattered light either emit from the first aperture to be measured with a spectrometer device, or are re-scattered by the sample at the second aperture. The multi-reflection of the reflective cavity greatly improves the excitation efficiency of Raman scattering from the sample and in the meantime enhances its collection efficiency. In addition, it also causes more excitation light to penetrate into a diffusely scattering sample and allows efficient collection of the Raman scattered light generated thereof, hence enabling sub-surface Raman scattering measurement.

BRIEF DESCRIPTION OF THE FIGURES

The accompanying FIGS., where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1A:
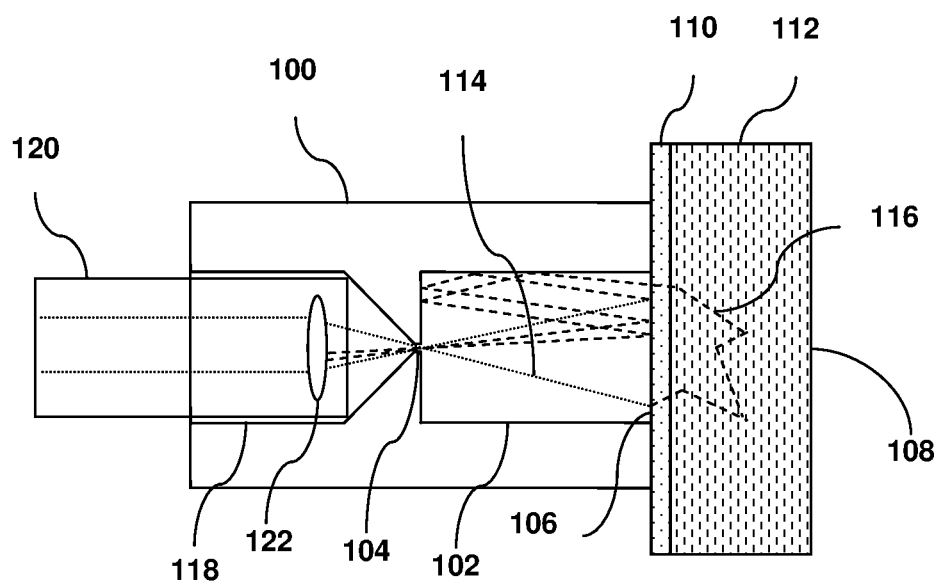
FIGS. 1A-C illustrate a first exemplary embodiment of the light delivery and collection device having a reflective cavity for Raman scattering excitation and collection as well as a receptacle for receiving a probe.

Skilled artisans will appreciate that elements in the FIGS. are illustrated for simplicity and clarity and have not necessarily been drawn to scale. For example, the dimensions of some of the elements in the FIGS. may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a light delivery and collection device for measuring Raman scattering of a sample. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1a illustrates a first exemplary embodiment of the light delivery and collection device, which is configured to deliver excitation light to a large area of a sample and collect the Raman scattered light generated thereof. The light delivery and collection device 100 comprises a reflective cavity 102 which is made of a material with high reflectivity to the excitation light and the Raman scattered light. Such material can be metal materials, e.g. gold, silver, copper, and aluminum, etc. Or it can be dielectric materials, preferably particles of dielectric materials which are firmly packed together. The dielectric material is transparent or translucent to the excitation light and the Raman scattering light and reflects the light through multiple reflection at the boundary of the particles or through diffuse scattering inside the translucent material. The surface of the reflective cavity is preferably polished to increase its reflectivity. Alternatively, the reflective cavity 102 may have a surface coating with high reflectivity to the excitation light and the Raman scattered light. Such surface coating can be a metal coating which exhibits high reflection in a broad range of wavelengths. Or it can be a dielectric coating, which has a customized reflection wavelength range. The latter one may reflect only the wavelengths of interest thus rejecting stray light or fluorescence light which does not overlap with the excitation light and the Raman scattered light in wavelength.

The light delivery and collection device 100 further comprises a receptacle 118 which is configured to receive a probe 120. The probe 120 comprises one or more optical components 122, such as optical lenses, mirrors, filters, beam splitters, optical fibers, etc., which receive excitation light from a light source, such as a laser light source (not shown) and focus the excitation light at a first aperture 104 of the reflective cavity 102 and thereby deliver the excitation light 114 into the reflective cavity 102. The aperture 104 preferably has a size as small as possible, but large enough to pass unobstructed the excitation light and Raman light collectable by the probe 120. The excitation light 114 diverges and projects onto a second aperture 106 of the reflective cavity 102, which preferably has a size much larger than the first aperture 104, and more preferably, at least 2 times as large as the first aperture 104 in area and covering an area of at least a few square millimeters. The second aperture 106 of the reflective cavity 102 is configured to be applied close to the sample 108 such that the reflective cavity 102 substantially forms an enclosure covering a large area of the sample 108, where the excitation light 114 produces Raman scattered light 116 from the covered area of the sample 108. By collecting the Raman scattering from a large volume of the sample, the excitation light intensity on the sample is reduced to avoid sample damage. In the meantime, the collected Raman spectrum is more representative, especially for non-uniform samples. Here the sample 108 can be diffusely scattering samples, such as pharmaceuticals, powders, biological tissues, etc. or even samples having multiple layers of different materials. In the example as shown in FIG. 1a, the sample 108 is a diffusely scattering sample having a surface layer 110 and a sub-surface layer 112, e.g. a container with powders inside. The sample 108 scatters the excitation light 114, either through elastic scattering or inelastic scattering, i.e. Raman scattering back into the reflective cavity 102. The reflective cavity 102 reflects any excitation light and Raman scattered light scattered from the sample unless the excitation light and the Raman scattered light either emit from the first aperture 104 to be collected by the probe 120 and then measured with a spectrometer device (not shown) to obtain a Raman spectrum of the sample 108, or are re-scattered by the sample 108 at the second aperture 106. The multi-reflection of the reflective cavity greatly improves the excitation efficiency of Raman scattering from the sample and in the meantime enhances its collection efficiency. In this example, the excitation light 114 penetrates through the surface layer 110 of the sample 108 with the aid of the reflective cavity 102 and produces Raman scattering from the sub-surface layer 112 of the sample 108. Hence the measured Raman spectrum contains the characteristic information of both the surface layer 110 and the sub-surface layer 112 of the sample 108. In a separate step, the light delivery and collection device 100 can be removed and the excitation light from the probe 120 is directly focused onto the surface layer 110 of the sample 108 to measure a Raman spectrum of the surface layer 110. The latter Raman spectrum can be mathematically extracted from the previously measured Raman spectrum to obtain a Raman spectrum of the sub-surface layer of the sample. The enhanced excitation and collection efficiency of the Raman scattered light as provided by the reflective cavity hence enables sub-surface Raman scattering measurement.

Figure 1B:
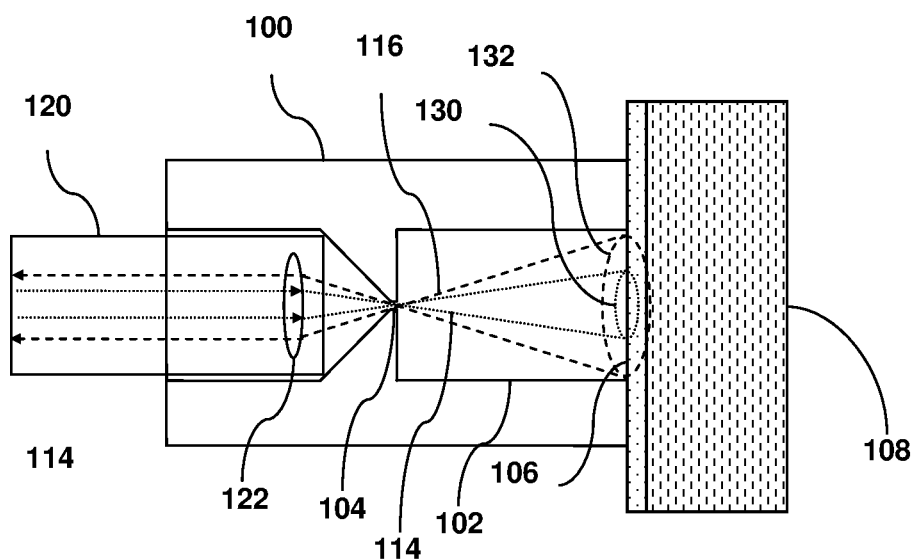
Figure 1C:
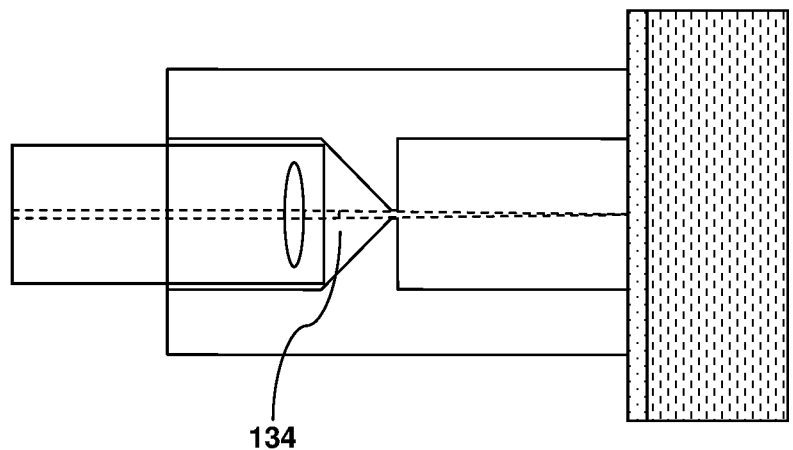

Optically, the reflective cavity serves three purposes, including (i) to provide a large sampling area; (ii) to maximize signal collection by means of multiple reflection and scattering as explained previously; and (iii) to isolate the sampled area from ambient light which would otherwise contaminate the signal. The size of the sampling area should be determined by the specific sampling requirement. For example, if the sample is heterogeneous and the goal is to obtain a better representation of the sample in whole, the sampling area should be made at least several times larger than the grain size. If the purpose is to measure sub-surface sample through a layer of packaging material, then the linear size of the sampling area should be several times the thickness of the packaging material. With the desired sampling area determined, FIG. 1b further illustrates the design considerations of the reflective cavity to achieve maximum signal collection. The excitation light beam 114 from the probe 120 is focused by the optical components 122 at the first aperture 104, and then diverges and projects onto the second aperture 106, covering an initial illumination area 130. The light beam 116 collectable by the probe optics similarly projects a collection area 132. The collection area 132 and the initial illumination area 130 may be different in size. With the probe optics fixed, the minimum size of the first aperture 104 and the divergence angles of both beams are determined. For maximum collection efficiency, the size of the first aperture 104 should be made as small as possible without obstructing the excitation and collection beams, that is, just large enough to encircle their beam waists at the first aperture 104. If it is made much larger, scattered excitation light and Raman light falling on the area outside the collection beam waist but inside the first aperture will exit the first aperture 104 without being collected by the probe 120. To determine the size of the second aperture 106 for maximum signal collection, one shall first consider that the light outside the aperture is blocked, so the aperture should be at least the size of the desired sampling area. Next the inevitable loss at each reflection by the reflective cavity 102 and at each scattering by the sample 108 must be considered. For maximum collection efficiency, the Raman scattered light should be allowed to exit the first aperture 104 and to be collected by the probe 120 by going through as few rounds of reflection and scattering as possible. If the second aperture 106 is made larger than the projected area 132, Raman light emerging from the area outside the projected area 132 cannot be captured by the probe 120 without going through more reflection and scattering, which will result in reduced efficiency and limit the effective sampling area to area 132. Therefore the sampling area is the smaller of area 132 and the second aperture 106. On the other hand, the angle of collection 134 as shown in FIG. 1c for signal light from the second aperture 106 is proportional to the collection beam size at the first aperture 104, and inversely proportional to the cavity length. The larger this angle is, the higher the collection efficiency. Therefore, the cavity length should be made as short as possible, without reducing the projected area 132 to below the required sampling area. These factors combine to provide that for optimal efficiency, the size of the second aperture 106 should be equal to the desired sampling area, and that the cavity length should be such that the projected area 132 is equal to the size of the second aperture 106.

Preferably, the second aperture 106 of the reflective cavity 102 is at least 2 times as large as the first aperture 104 in area.

Figure 2:
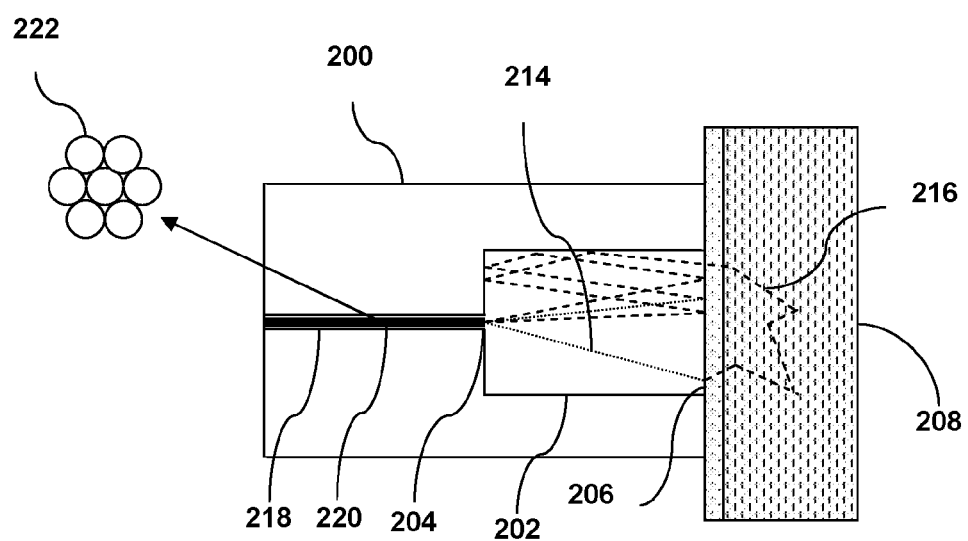
FIG. 2 illustrates a second exemplary embodiment of the light delivery and collection device having a reflective cavity for Raman scattering excitation and collection as well as a receptacle for receiving an optical fiber or fiber bundle.

FIG. 2 illustrates a second exemplary embodiment of the light delivery and collection device. Here the light delivery and collection device 200 comprises a reflective cavity 202 having a similar structure as the reflective cavity 102 in FIG. 1, as well as a receptacle 218 which is configured to receive one or more optical fibers or fiber bundles 220. The optical fiber or fiber bundle terminates at the proximity of a first aperture 204 of the reflective cavity 202 so as to deliver the excitation light from a light source (not shown) into the reflective cavity 202. In a similar way as shown in FIG. 1, the excitation light 214 excites Raman scattering from the sample 208 at a second aperture 206 of the reflective cavity 202. The reflective cavity 202 reflects any excitation light and Raman scattered light 216 scattered from the sample unless the excitation light and the Raman scattered light 216 either emit from the first aperture 204 to be collected by the fibers 220 and then measured with a spectrometer device (not shown) to obtain a Raman spectrum of the sample 208, or are re-scattered by the sample 208 at the second aperture 206. The fiber bundle 220 may comprise multiple optical fibers 222. A portion of the fibers, e.g. the fiber in the center of the bundle may be used for delivering the excitation light while the other portion of the fibers, e.g. the fibers at the periphery of the bundle may be used for collecting the Raman scattered light.

Figure 3:
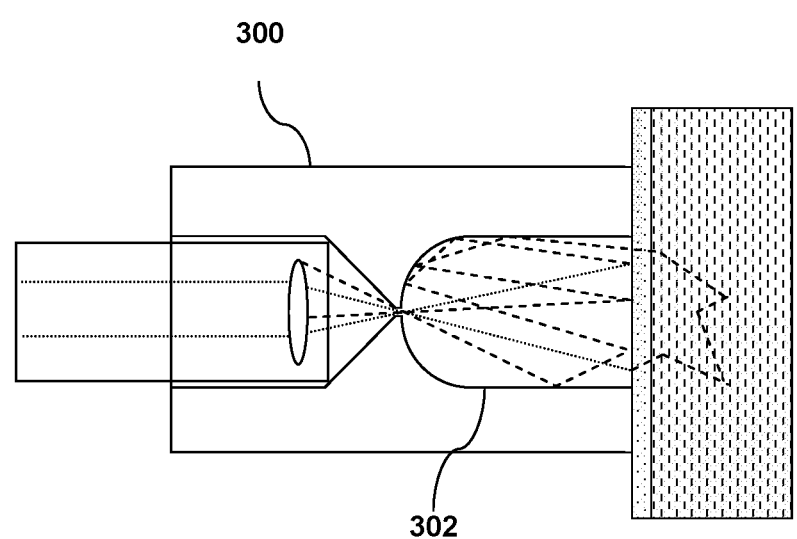
FIG. 3 illustrates a variation of the first exemplary embodiment of the light delivery and collection device, which has a differently shaped reflective cavity.

The reflective cavity of the light delivery and collection device may take different shapes. In a slight variation of the light delivery and collection device as shown in FIG. 3, the reflective cavity 302 of the light delivery and collection device 300 is spherically or paraboloidal shaped. The special shape may favorably reflect the light into certain directions hence increasing the excitation and collection efficiency of the Raman scattering in those directions.

In yet another variation of the light delivery and collection device, the reflective cavity may have an additional aperture for outputting the Raman scattered light. The position of this aperture on the reflective cavity may be optimized, for example, to minimize the collected percentage of the Raman scattering signal from the surface material of the sample and maximize the collected percentage of the Raman scattering signal from the sub-surface material of the sample. Alternatively, the additional aperture may be used to deliver another excitation light of different wavelength to excite Raman scattering from the sample.

Figure 4:
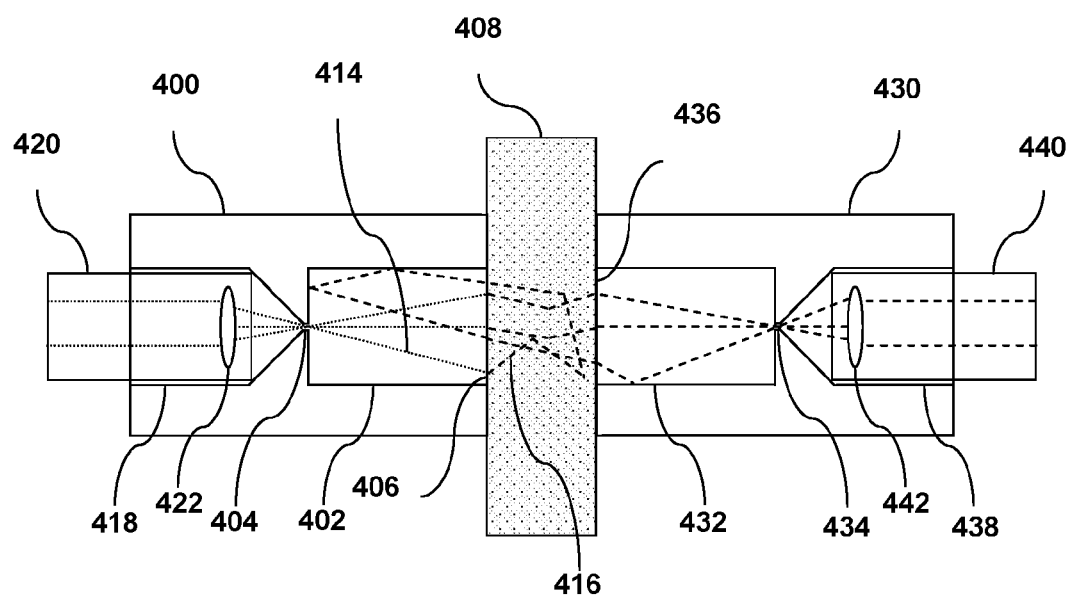
FIG. 4 illustrates a scheme of utilizing the first exemplary embodiment of the light delivery and collection device for measuring the transmissive Raman scattering of a diffusely scattering sample.

FIG. 4 illustrates a scheme of utilizing the first exemplary embodiment of the light delivery and collection device for measuring the transmissive Raman scattering of a diffusely scattering sample. In this example, two of such devices are utilized. One device is used for delivering the excitation light to one side of the sample and another device is used for collecting the Raman scattered light from the opposite side of the sample. Referring to FIG. 4, the light delivery device 400 has a receptacle 418 to receive a probe 420 and a reflective cavity 402 with its first aperture 404 in communication with the probe 420 to receive the excitation light 414. The second aperture 406 of the light delivery device 400 is applied close to one side of the sample 408 such that the reflective cavity 402 of the light delivery device 400 substantially forms an enclosure covering a large area of the sample to excite Raman scattered light 416 thereof. The light collection device 430 has a reflective cavity 432 with its second aperture 436 applied onto the opposite side of the sample 408 such that the reflective cavity 432 collects the Raman scattered light that transmits through the sample 408 and delivers it through the first aperture 434 of the reflective cavity 432 to a probe 440 to be analyzed by a spectrometer device (not shown). The reflective cavity 402 of the light delivery device 400 enhances the Raman excitation and collection efficiency by reflecting back into the sample the majority of excitation light and Raman scattered light that are scattered back by the sample until they transmits through the sample. The reflective cavity 432 of the light delivery device 430 functions similarly by reflecting back any excitation light and Raman scattered light that do not fall on its exit aperture, i.e. the first aperture 434. In a slight variation of the present scheme, the light delivery device 400 may also be used for collecting the back scattered Raman light from the sample 408 in a similar way as shown in FIG. 1. The spectrum of the back scattered Raman light and the forward scattered Raman light may be used together to analyze the composition of the sample 408.

Figure 5:
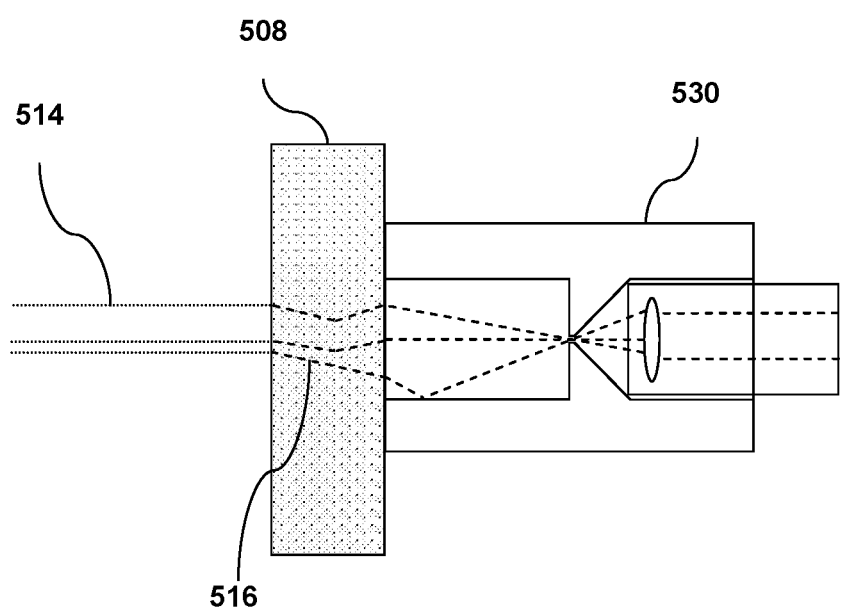
FIG. 5 illustrates a slightly different scheme of utilizing the first exemplary embodiment of the light delivery and collection device for measuring the transmissive Raman scattering of a diffusely scattering sample.

FIG. 5 illustrates a slightly different scheme of utilizing the first exemplary embodiment of the light delivery and collection device for measuring the transmissive Raman scattering of a diffusely scattering sample. Here the excitation light 514 is directly delivered onto one side of the sample 508 to excite Raman scattered light 516 from the sample. The excitation light 514 can be either collimated, or converging, or diverging. A light collection device 530 with similar design as shown in FIG. 1 is employed to collect the Raman scattered light 516 that transmits through the sample 508.

In a similar manner, the light delivery and collection device as shown FIG. 2 and FIG. 3 may be used for measuring the transmissive Raman scattering of transparent or diffusely scattering samples.

FIG. 6 and FIG. 7 show two examples of utilizing the light delivery and collection device for measuring the Raman spectra of diffusely scattering samples contained in diffusely scattering containers.

Figures 6A, 6B, 6C, 6D:
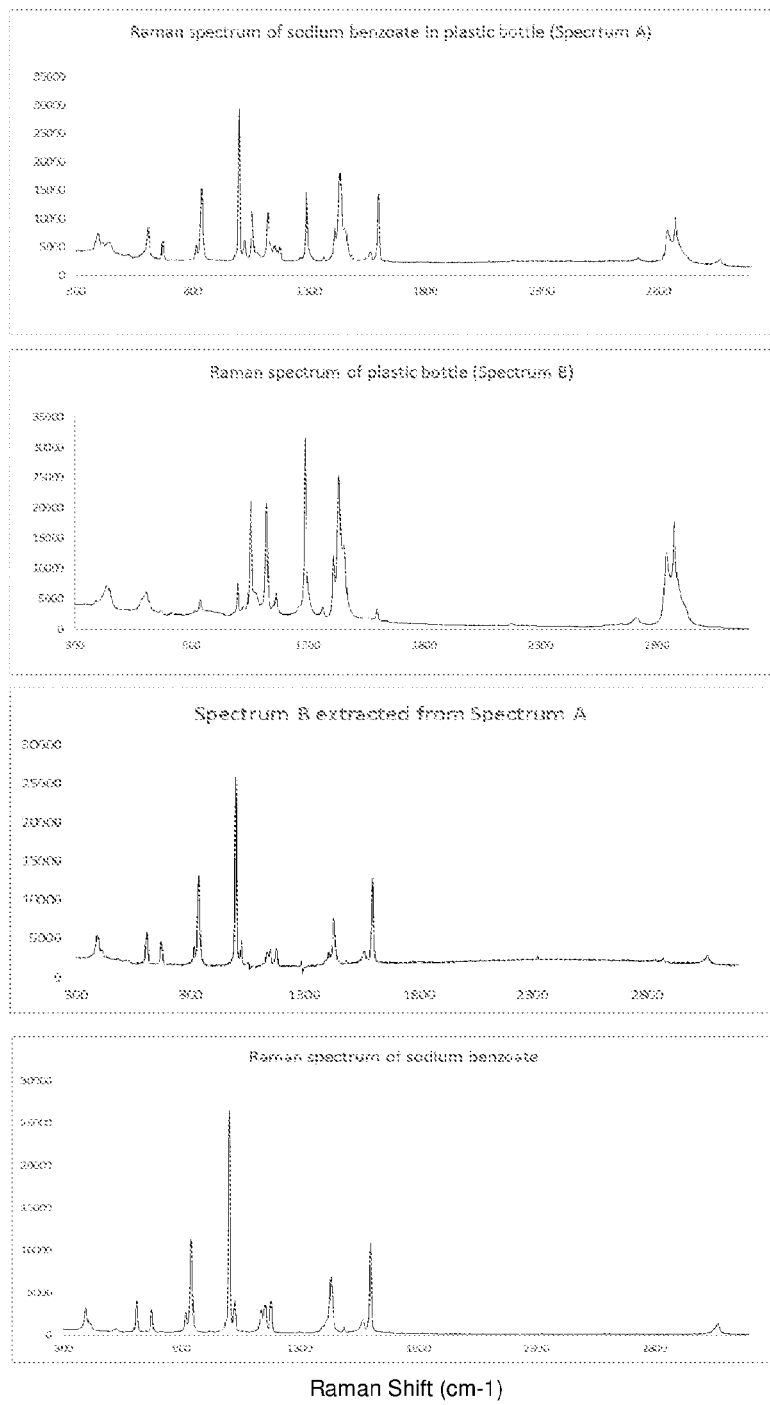
FIGS. 6A-D show the measured Raman spectrum of a sodium benzoate sample contained in a plastic bottle, as well as the Raman spectrum of the plastic bottle and the Raman spectrum of the sodium benzoate sample for comparison.

FIG. 6a shows the Raman spectrum of sodium benzoate powder contained in a white plastic bottle, which is measured with the aid of a light delivery and collection device as shown in FIG. 1. FIG. 6b shows the measured Raman spectrum of the plastic bottle by removing the light delivery and collection device and focusing the laser beam directly on the surface of the plastic bottle. By properly scaling the spectrum in FIG. 6b and then subtracting the scaled spectrum from the spectrum in FIG. 6a, one can obtain a calculated Raman spectrum of the sodium benzoate powder as shown in FIG. 6c. Comparing this spectrum with the Raman spectrum shown in FIG. 6d, which is collected directly from purely sodium benzoate powder, it can be seen that the calculated spectrum is close enough to the spectrum of the pure sodium benzoate powder. By optimizing the mathematical algorithm in extracting the spectrum of the container, it is possible to further improve the quality of the obtained spectrum of the sample.

Alternatively, mixture analysis can be performed directly using spectrum in FIG. 6a to identify the material makeup of the sample as a whole, including the container and the content inside. Various mixture spectral analysis algorithms exist to accomplish such tasks. With prior knowledge of the container material, the chemical composition of the content inside can be determined. In yet another implementation, the container spectrum in FIG. 6b can be designated as a component, and a modified mixture analysis method can be used to identify the remaining component that make up the spectrum FIG. 6a.

Figures 7A, 7B, 7C:
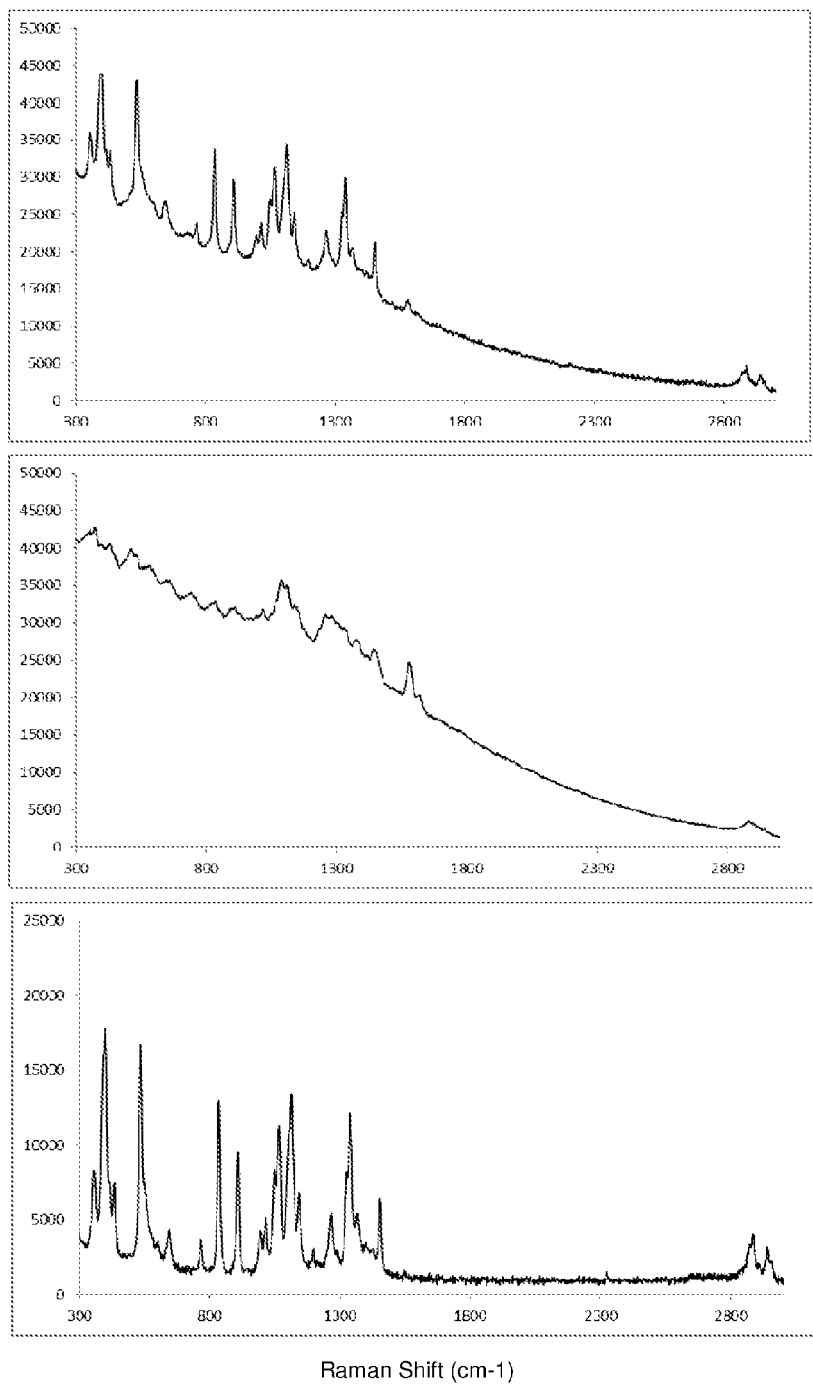
FIGS. 7A-C show the measured Raman spectrum of a D(+)-Glucose sample contained in a brown envelope, as well as the Raman spectrum of the brown envelope and the Raman spectrum of the D(+)-Glucose sample for comparison.

FIG. 7 illustrates how the light delivery and collection device enable material identification by means of Raman spectroscopy through a different kind of packaging material, i. e. a brown paper envelope. FIG. 7a shows the Raman spectrum of a D(+)-Glucose sample contained in the brown envelope measured with the aid of a light delivery and collection device as shown in FIG. 1. FIG. 7b shows the Raman spectrum obtained without the device and with the excitation beam focused on the brown envelope. FIG. 7a shows the Raman spectrum of the D(+)-Glucose sample obtained without the brown paper envelope. Here the brown envelope spectrum in FIG. 7b displays the signature of cellulose on top of a high level of fluorescence. The signature of the glucose content is almost completely absent. In contrast, the Raman spectrum obtained with the light delivery and collection device is almost entirely of D(+)-Glucose, with a relatively weak contribution from the cellulose. In this case, the material inside the packaging material can be directly identified by searching through a spectral library.

Figures 8A, 8B, 8C:
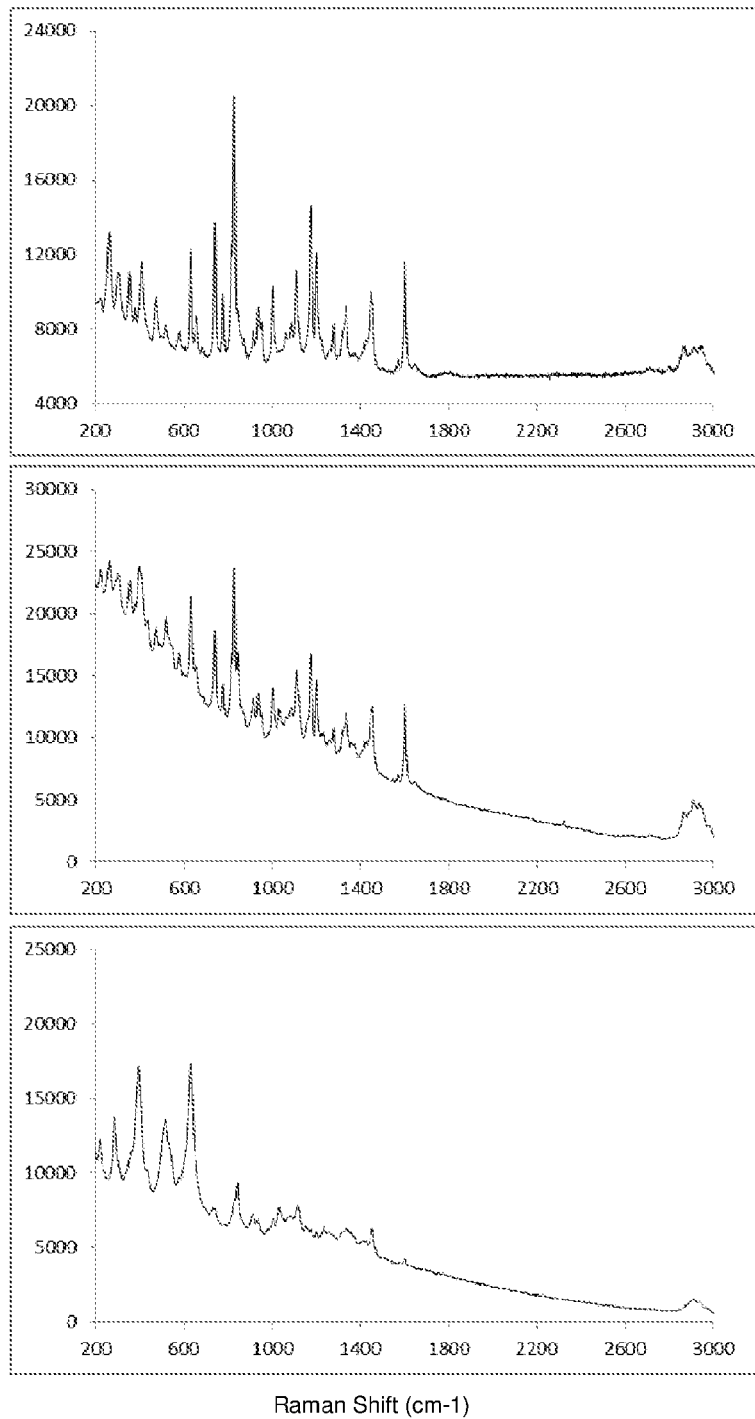
FIGS. 8A-C show the Raman spectrum of a coated ibuprofen tablet sample obtained in three different measurement modes.

FIG. 8 illustrates how the light delivery and collection device used in transmission mode enables the measurement of bulk material property. Here the sample is an ibuprofen tablet (Advil, 200 mg) purchased from a local drug store. The tablet has a brown colored coating. The spectrum in FIG. 8a is obtained in transmission mode using the configuration shown in FIG. 4; the spectrum in FIG. 8b is obtained in reflection mode using the configuration shown in FIG. 1; and the spectrum in FIG. 8c is obtained in reflection mode without the aid of the light delivery and collection device. The spectrum in FIG. 8c consists of features mostly from the coating of the tablet, while the transmissive Raman spectrum in FIG. 8a consists almost entirely of the drug material inside the coating. The spectrum in FIG. 8b is similar to the spectrum in FIG. 8a, but has relatively more contribution from the coating. To those skilled in the art, it is known that the transmission mode measures the Raman signal throughout the entire thickness of the sample, therefore is more advantageous when the bulk property of the sample as a whole is of interest.

In the foregoing specification, specific embodiments of the present invention have been described. However, one of ordinary skill in the art appreciates that various modifications and changes can be made without departing from the scope of the present invention as set forth in the claims below. Accordingly, the specification and FIGS. are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A light delivery and collection device for measuring Raman scattering from an area of a sample, the light delivery and collection device comprising:
    a reflective cavity having a first aperture and a second aperture, the second aperture configured to be applied to the sample such that the reflective cavity substantially forms an enclosure covering an area of the sample; and
    one or more optic components which receive excitation light from a light source and focus the excitation light at the first aperture of the reflective cavity to deliver the excitation into the reflective cavity, wherein the excitation light projects onto the second aperture of the reflective cavity and is scattered by the covered area of the sample to generate Raman light,
    wherein the reflective cavity is adapted to reflect back-scattered excitation light and Raman light and causes said back-scattered excitation light and Raman light to be re-scattered by the sample at the second aperture, except said back-scattered excitation light and Raman light that exits the reflective cavity through the first aperture to be collected by the one or more optic components for measurement, and
    wherein the first aperture is sized substantially just large enough to encompass the beam waist of the focused excitation light.

2. The light delivery and collection device of claim 1, wherein the reflective cavity is made of a material having high reflectivity to the excitation light and the Raman light.

3. The light delivery and collection device of claim 1, wherein the reflective cavity has a surface coating with high reflectivity to the excitation light and the Raman light.

4. The light delivery and collection device of claim 3, wherein the surface coating is a metal coating.

5. The light delivery and collection device of claim 3, wherein the surface coating is a dielectric coating.

6. The light delivery and collection device of claim 1, wherein the reflective cavity comprises at least one additional aperture.

7. The light delivery and collection device of claim 1, wherein the second aperture of the reflective cavity is at least 2 times as large as the first aperture in area.

8. A method for measuring Raman scattering from an area of a sample, the method comprising the steps of:
    providing a reflective cavity having a first aperture and a second aperture;
    applying the second aperture of the reflective cavity to the sample such that the reflective cavity substantially forms an enclosure covering an area of the sample;
    providing one or more optic components which receive excitation light from a light source and focus the excitation light at the first aperture of the reflective cavity to deliver the excitation into the reflective cavity, wherein the excitation light projects onto the second aperture of the reflective cavity and is scattered by the covered area of the sample to generate Raman light, and wherein the reflective cavity reflects back-scattered excitation light and Raman light and causes said back-scattered excitation light and Raman light to be re-scattered by the sample at the second aperture, except said back-scattered excitation light and Raman light that exits the reflective cavity through the first aperture to be collected by the one or more optic components, and wherein the first aperture is sized substantially just large enough to encompass the beam waist of the focused excitation light; and measuring the Raman light collected by the one or more optic components to obtain a Raman spectrum of the sample.

9. The method of claim 8, wherein the reflective cavity is made of a material having high reflectivity to the excitation light and the Raman light.

10. The method of claim 8, wherein the reflective cavity has a surface coating with high reflectivity to the excitation light and the Raman light.

11. The method of claim 10, wherein the surface coating is a metal coating.

12. The method of claim 10, wherein the surface coating is a dielectric coating.

13. The method of claim 8, wherein the second aperture is at least 2 times as large as the first aperture in area.

14. A method for analyzing a diffusely scattering sample having a surface layer and a sub-surface layer of different materials, the method comprising the steps of:

providing a reflective cavity having a first aperture and a second aperture;

applying the second aperture of the reflective cavity to the sample such that the reflective cavity substantially forms an enclosure covering an area of the sample;

delivering excitation light through the first aperture to be projected onto the second aperture of the reflective cavity, wherein the excitation light is scattered by the covered area of the sample to generate Raman light, and wherein the reflective cavity reflects back-scattered excitation light and Raman light and causes said back-scattered excitation light and Raman light to be re-scattered by the sample at the second aperture, except said back-scattered excitation light and Raman light that exits the reflective cavity through the first aperture, wherein the first aperture is sized substantially just large enough to encompass the beam waist of the excitation light;

measuring the Raman light emitted from the first aperture of the reflective cavity to obtain a first Raman spectrum of the sample which contains signatures of both the surface layer and the sub-surface layer of the sample;

removing the light delivery and collection device and focusing the excitation light to the surface layer of the sample to excite Raman light from the surface layer, and measuring the Raman light from the surface layer to obtain a second Raman spectrum of the sample which mainly contains signatures of the surface layer of the sample; and analyzing a difference between the first Raman spectrum and the second Raman spectrum to identify the material of the sub-surface layer.

15. A method for measuring Raman scattering of a transparent or diffusely scattering sample, the method comprising the steps of:

delivering excitation light onto a first side of the sample to generate Raman light;

providing a first reflective cavity having a first aperture and a second aperture;

applying the second aperture of the first reflective cavity to a second side opposite to the first side of the sample such that the first reflective cavity substantially forms an enclosure covering an area on the second side of the sample, wherein the excitation light and Raman light at least partially transmits from the first side to the second side of the sample, and the first reflective cavity reflects said transmitted excitation light and Raman light and causes said transmitted excitation light and Raman light to be re-scattered by the sample, except said transmitted excitation light and Raman light that exits the first reflective cavity through the first aperture of the first reflective cavity, and wherein the first aperture is sized substantially just large enough to encompass the beam waist of the excitation light; and measuring the Raman light emitted from the first aperture of the first reflective cavity to obtain a Raman spectrum of the sample.

16. The method of claim 15, wherein the step of delivering excitation light onto a first side of the sample to generate Raman light comprises the steps of:

providing a second reflective cavity having a first aperture and a second aperture;

applying the second aperture of the second reflective cavity to the first side of the sample such that the second reflective cavity substantially forms an enclosure covering an area on the first side of the sample; and delivering t h e excitation light through the first aperture of the second reflective cavity to be projected onto the second aperture of the second reflective cavity, wherein the excitation light is scattered by the covered area on the first side of the sample to generate Raman light, and wherein the second reflective cavity reflects back-scattered excitation light and Raman light and causes said back-scattered excitation light and Raman light to be re-scattered by the sample at the second aperture of the second reflective cavity, except said back-scattered excitation light and Raman light that exits the second reflective cavity through the first aperture of the second reflective cavity.

17. A light delivery and collection device for measuring Raman scattering from an area of a sample, the light delivery and collection device comprising:

a reflective cavity having a first aperture and a second aperture, wherein the second aperture is configured to be applied to the sample such that the reflective cavity substantially forms an enclosure covering an area of the sample; and one or more optic components adapted to receive excitation light from a light source and focus the excitation light at the first aperture of the reflective cavity to deliver the excitation into the reflective cavity, wherein the excitation light projects onto the second aperture and has a projected area greater than the first aperture and less than or equal to the second aperture, and wherein the first aperture is sized substantially just large enough to encompass the beam waist of the focused excitation light.

* * * * *